United States Patent

Lakusiewicz

Patent Number: 5,842,970
Date of Patent: Dec. 1, 1998

[54] NON-SURGICAL EXTERNAL PENILE PROSTHETIC DEVICE

[76] Inventor: Ronald J. Lakusiewicz, 1316 Euel Rd., Poplar Bluff, Mo. 63901

[21] Appl. No.: 890,820

[22] Filed: Jul. 10, 1997

[51] Int. Cl.[6] .................................. A61F 5/00; A61F 6/02
[52] U.S. Cl. .............................................. 600/38; 128/844
[58] Field of Search .................................. 600/38–41, 33, 600/35; 128/842, 844; 601/46, 48

[56] References Cited

U.S. PATENT DOCUMENTS

| 4,432,357 | 2/1984 | Pomeranz . | |
| 5,483,697 | 1/1996 | Fuchs | 2/161.7 |
| 5,623,945 | 4/1997 | Shecterle et al. | 128/842 |
| 5,662,186 | 9/1997 | Schwartz | 128/842 |
| 5,666,971 | 9/1997 | Anatolievich | 128/842 |

FOREIGN PATENT DOCUMENTS 404161150  6/1990  Japan ........................................ 600/39

*Primary Examiner*—Jennifer Bahr
*Assistant Examiner*—Roy D. Gibson
*Attorney, Agent, or Firm*—Peper, Martin, et al.

[57] ABSTRACT

An external penile prosthetic device is adapted to be worn on the groin and suprapubic areas of the wearer. The device has a generally tubular outer wall made from a flexible material, having an open proximal end and a closed distal end, the exterior of the outer wall being configured to resemble an erect human penis. The device also has a generally tubular inner wall made from a flexible material having a different degree of duramater firmness than that of the outer wall and an open proximal end and a closed distal end. The inner wall is disposed spacedly and coaxially inside the outer wall and is sealed thereto at least at their respective proximal ends to define a chamber therebetween. A viscous fluid fills the chamber between the outer wall and the inner wall. A flange is disposed around and connected to the proximal end of the outer wall of the prosthetic device for mounting the device over the groin and suprapubic areas of the wearer.

21 Claims, 4 Drawing Sheets

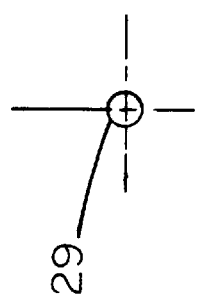
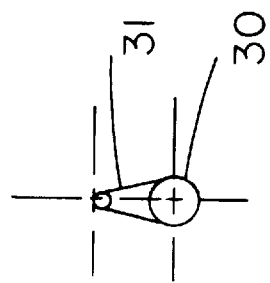
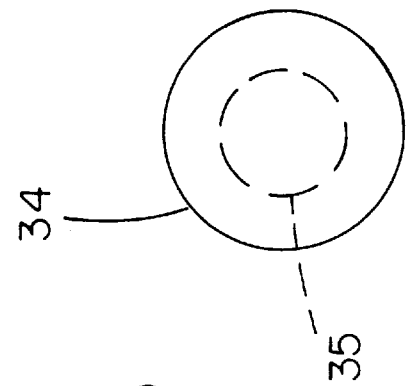
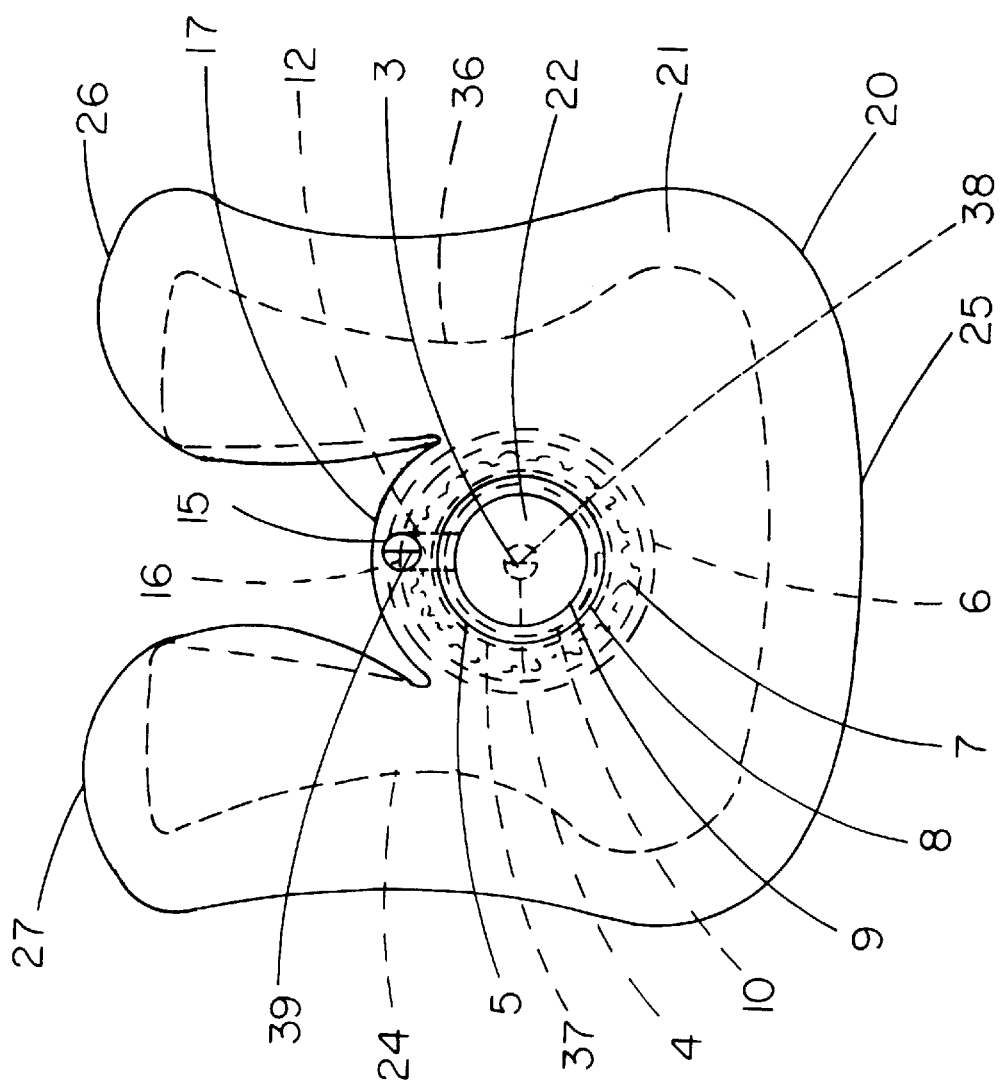
FIG. 9
FIG. 10
FIG. 11
FIG. 8

NON-SURGICAL EXTERNAL PENILE PROSTHETIC DEVICE

FIELD OF INVENTION

This invention relates to an external prosthetic device adapted to be worn incorporating the penis to eliminate the problem of inability to either obtain, or sustain, an erection, which is impotence by definition.

BACKGROUND AND SUMMARY OF THE INVENTION

The present invention external prosthetic device adapted to be worn incorporating the penis in order to alleviate problems of erection, termed impotence. The invention is formed substantially entirely silicone in various forms, that when combined together produce a realistic, natural looking erect penis externally, that has multiple cylindrical walls fitting inside one another, separated by totally enveloped silicon gel that is allowed free flow in and around the inner wall and into the terminal end of the device. The silicone gel, upon flowing into the terminal end of the device, driven by manual or external compression of the shaft of the device, creates pressure on a spherical wall which is then able to evacuate the contents of its chamber through a narrow slit opening at the tip of the device. The penile device internal wall and the outer total containment wall are fused into one conically shaped smooth flange for attachment to the body by a strong medical adhesive. The attachment flange is strongly re-enforced by thickened silicone in the anterior-superior pubic portion and two lateral lobes for attachment to the adductor groin regions. The posterior portion of the flange is cutaway to eliminate testicular pressure and has only a narrow bridge of thickened silicone which makes up the posterior wall of the total containment wall and contains a tunnel that communicates with the distal end of the inner wall. A flexible silicone rod inserted into this tunnel exits through the end of the inner wall turns upon itself with progressive insertion and then is withdrawn out of the inner wall so that while the flexible rod is fully within the device, both of its ends are protruding externally. The flaccid penis is then attached by tape to the end of the flexible rod protruding from the inner wall and by pulling on the end of the flexible rod protruding from the posterior tunnel is drawn into the inner chamber the full length of the penis. With the flexible rod now totally removed along with the tapes that pull free, the attachment flanges are sprayed with a strong medical adhesive and attachment is secure without belts of any kind and with a device that looks completely natural like the normal body part. The device is therefore able to provide an erection for a totally flaccid penis whatever its cause; is able to produce ejaculation of whatever contents are present in the spherical chamber; and also functions protectively as a condom, such that problems of erection, artificial insemination in a more natural way, and protection against pregnancy and disease are all addressed.

The National Institutes of Health (NIH) estimates that 30 million American men are affected by the extremely common medical condition known as impotence. In addition, the Journal of Sex and Marital Therapy found that although 97% of men in their study had one or more sexual concerns, that only 23% reported that their physician had ever inquired; only 25% of the patients had ever raised sexual questions themselves, yet 85% hoped their doctor would raise such issues. These findings make impotence the most untreated, treatable medical disorder in the United States. If the impotence totals of other countries of the world are also considered, then the overall problem of impotence worldwide is immense along with all the subordinate marital and social problems that impotence fosters.

There are many causes of impotence, some of which are the following:

Vascular: (arteriosclerosis, venous deficiency)
Endocrine:
  Hypogonodism
  Hyperprolactinemia
  Thyroid deficiency or excess
  Diabetes mellitus
Neuropathy
*Medications
Alcoholism
Systemic Disease
Psychological Factors
Urologic Disorders
Age Of the *Medications commonly associated with impotence, we see that those used to treat very common conditions such as:

High Blood Pressure (Anti-Hypertensives)
Fluid Retention (Diuretics)
Nervous Disorders (Tranquilizers)
Heart Disease (Digoxin)
Depression (Anti-Depressants)
High Blood Lipids (Gemfibrozil)
Arthritis (Non-Steroidal Anti-Inflammatories)
Anti-Convulsants
Others are commonly implicated in producing impotence.

While any person who becomes impotent should have a thorough medical examination for the underlying cause of the impotence, all of the aforementioned causes of impotence produce the same end point relative to the penis regardless of the cause and that is the inability to obtain or sustain an erection, which is the definition of impotence per se. Therefore, this invention, —the external penile prosthetic device, was developed to address that end point rendering it immaterial to the wearer in terms of the wearer's ability to accomplish sexual intercourse.

Prior to the present invention, the management of impotence existed and still exists by the following methods; each of which has benefits, but also significant side effects and problems.

I. Mechanical Devices

1. Vacuum tumescence devices that produce erection by use of external negative pressure maintained by use of a rubber ring tourniquet around the base of the penis before removing the device. Its side effects include loss of penile rigidity, failure to ejaculate, pain, inconvenience of use and bruising.

II. Medications

1. Penile injections of papaverine or prostaglandin E1. Side effects are pain, bruising, urethral bleeding, scarring, fibrosis, and priapism that necessitates inserting larger needles into the penis to draw blood off.

2. Yohimbine whose side effects include hypertension and liver dysfunction.

3. Pentoxifylline, zinc, minoxidil, others, all partially effective.

4. Testosterone injections or transscrotal patch. Side effects of prostate enlargement, which may increase the rate of prostatic cancer growth; enlargement of male breasts (gynecomastia), liver dysfunction, and increased hemotocrit necessitating blood to be drawn off occasionally.

5. Insertion of pellets of Prostoglandin E1, into the urethra. Erection lasts about 20–40 minutes; but 30% of time an erection is not achieved even in males in whom it normally works. Side effects are penile pain and burning and since Prostoglandin E1, is present in the urethra it reaches the vagina during ejaculation and should not be used if the woman is pregnant.

III. Surgery

1. Internal Penile Devices such as bendable rods that are semi-rigid and inflatable rods. These devices carry with them all the possible complications of a surgical procedure and in addition, the inflatable devices have a 5 year survival rate of only 50%.

2. Surgical techniques to correct arterial blockage or venous leakage have varying success and are used only in cases where impotence has a vascular cause.

IV. External Penile Prosthetic Devices that contain the penis and have rigid bases pressed against the body and are attached by belts. These devices can be cumbersome and inconvenient to use and lack many other features of the present invention.

The present invention is different from all prior art and modes of therapy for impotence in that it is completely safe and has no side effects with use such as those present with injections, drug use, or surgery. It differs from other external devices in that it is not painful to use, requires no tourniquet at the base of the penis to maintain blood in the penile caverns, does not prevent ejaculation, and does not use belts to attach the device to the body. Cosmetically, the external surface of the outer wall is sculptured to appear as a normal penis and to feel like a normal erect penis; is made of multiple forms of silicone; attaches directly to the body by strong medical adhesive encasing the penis its full length in an inner chamber that contains irregular, crenulated firm silicone projections off the inner aspect of the cylindrically shaped inner wall that mimic the rugae of the vagina and stimulate the penis during intercourse. In a chamber between the semi-rigid inner wall and outer total containment wall resides a silicone gel. When the shaft of the present invention (which represents the shaft of the penis) is firmly squeezed, a positive pressure wave is created in the silicone gel which causes the get to flow into the distal end of the device that represents the head of the penis. The distal end of the device contains a cavity with a spherical wall, which when compressed by the positive pressure of the silicone gel, ejaculates the contents of the cavity through the tip of the penile device into the environment which is the vaginal vault. The firm, smooth attachment flange at the base of the device firmly secures the device to the symphysis pubis and adductor groin areas with strong medical adhesive such that with this flange covered by a plurality of filaments that are either real hair or polymer fibers, the device looks like a normal penis, not an artificial attachment piece.

The present invention is capable of addressing the four presentations of impotence which are:

1. Small penis (almost normal erection)
2. Partial unsustained erection
3. Flaccidity, no erection at all
4. No penis (from whatever cause)

The present invention is also capable of an ejaculation function not found in other penile devices, and therefore, can be used to actually inseminate the female during intercourse. If the desire of the wearer is not to inseminate, then the ejaculated sperm is totally contained in the inner chamber which now functions as a condom.

It is also possible for the present invention to deliver vaginal lubricant and medications from the spherical cavity into the vagina during intercourse.

It is an extremely important difference from prior art that this invention has a normal, natural appearance which helps to sexually arouse the female and give psychological confidence to the male resulting in a more normal sex act. Additionally, the male while engaged in intercourse "feels" as though he's in the actual vagina not a prosthetic device because of the rugae stimulation of the penis. These rugae provide a distinctive massage to the penis by the back and forth motion of the intercourse plus the intermittent squeezing of the penis by the female as this intermittent pressure is transmitted to the inner wall by the silicone gel and then to the penis by rugae in irregular intermittent impulses. The female "feels" both mentally and physically like she has a large, normal penis in her vagina. This helps to produce a state of heightened sexual intensity which is aimed at eliminating the psychogenic causes of impotence which ranks among its highest. Therefore, the present invention, (more closely than any other prior art), mimics the natural appearance and functions of the penis and relegates the impotence to irrelevancy regardless of its cause or presentation in the safest manner found to this date.

Accordingly, in furtherance of the above goals and advantages, the present invention is, briefly, an external penile prosthetic device adapted to be worn on the groin and suprapubic areas of the wearer. The device has a generally tubular outer wall made from a flexible material, having an open proximal end and a closed distal end, the exterior of the outer wall being configured to resemble an erect human penis. The device also has a generally tubular inner wall made from a flexible material. The inner wall has an open proximal end and a closed distal end, and is disposed spacedly and coaxially inside the outer wall and sealed thereto at least at their respective proximal ends to define a chamber therebetween. A viscous fluid fills the chamber between the outer wall and the inner wall. A flange is disposed around and connected to the proximal end of the outer wall of the prosthetic device for mounting the device over the groin and suprapubic areas of the wearer in a manner which does not impinge upon the blood vessels of the wearer.

The invention is further, briefly, a method of inserting a penis into a hollow elongate penile prosthetic device having an inner wall, an outer wall, and a passage extending between the inner wall and outer wall, the passage being open at the proximal end to the exterior of the prosthetic device, and at the distal end to the interior of the device, the method including the steps of: inserting a tether through the passage from the proximal end to the distal end, through the interior of the prosthetic device to the exterior; temporarily attaching the penis to the tether with at least two strips of tape on opposite sides of the penis; and pulling the tether to pull the penis into the prosthetic device.

The invention is also, briefly, a method of expelling contents from the external penile prosthetic device described, the device having a cavity in the distal end of the outer wall of the device, the cavity having a relatively large body and a narrow neck communicating with the exterior of the prosthetic device by a slit, the method including the steps of: applying a compressive force to the outer wall of the prosthetic device, transmitting the compressive force by the viscous fluid as a positive pressure fluid wave moving distally and coaxially in the chamber between the inner and outer walls of the prosthetic device; and collapsing the body of the cavity by the positive pressure fluid wave pushing cavity contents through the narrow neck and slit to the exterior of the prosthetic device, whereby the cavity can be filled with a preselected fluid and such fluid can be expelled at a preselected time to provide lubrication, medication and insemination, as suits the needs of the wearer of the device.

BRIEF DESCRIPTION OF THE DRAWINGS

FIG. 8 is a top end perspective view of the attachment flange of the external penile prosthetic device.

FIG. 9 is an end perspective view of the flexible rod of FIG. 6.

FIG. 10 is the top end perspective view of the stiff extraction rod of FIG. 7.

FIG. 11 is the top end perspective view of the solid obturator of FIG. 5.

Corresponding reference numerals indicate corresponding parts throughout the several views of the drawing.

DETAILED DESCRIPTION OF THE PREFERRED EMBODIMENT

Figure 1:
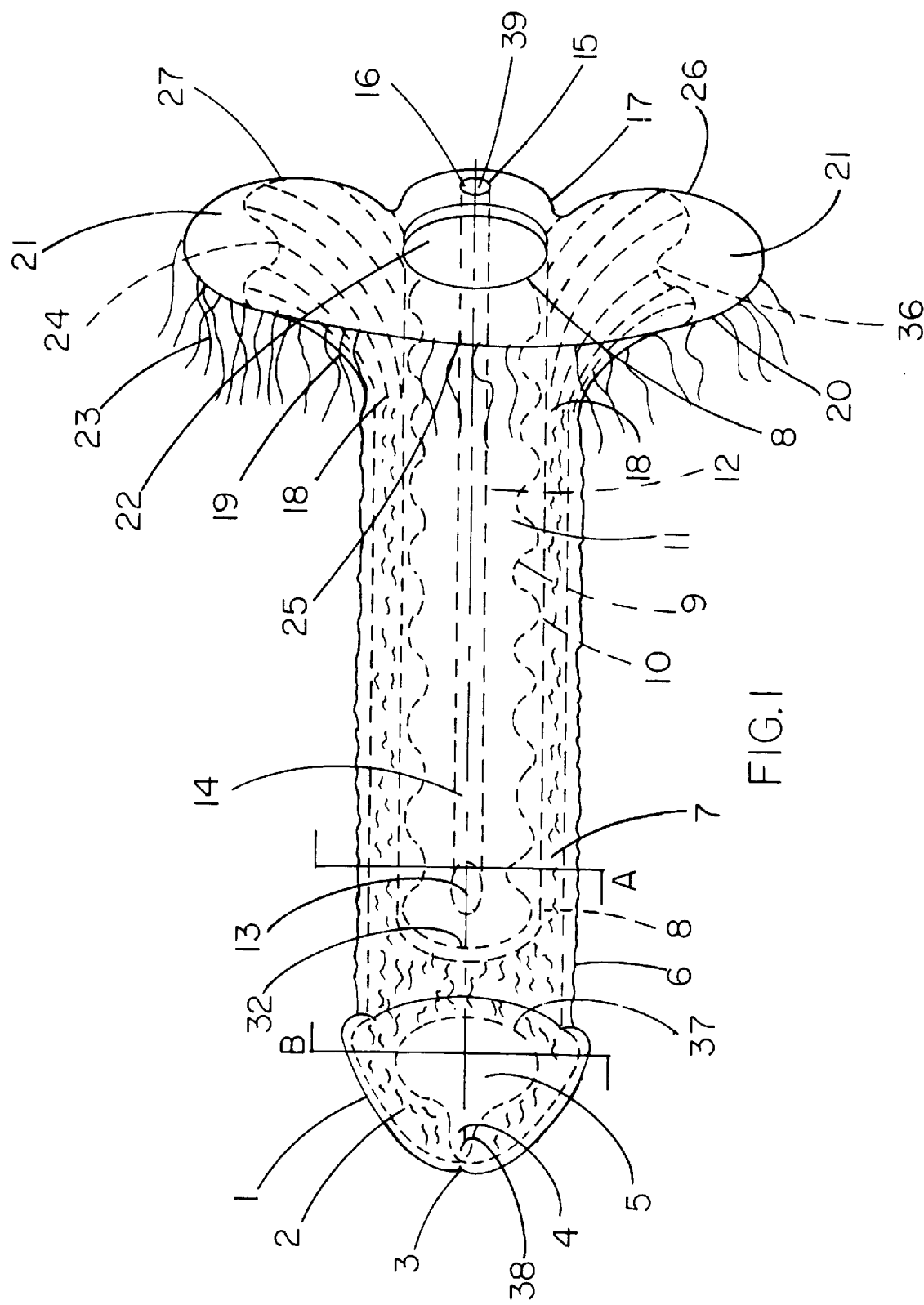
FIG. 1 is an anterior or front perspective view of the external penile prosthetic device constructed according to the principles of this invention.
Figure 2:
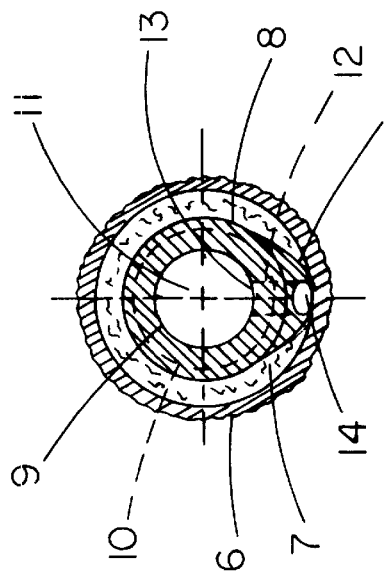
FIG. 2 is a cross-sectional perspective view of the external penile prosthetic device taken along the plane of line A.
Figure 3:
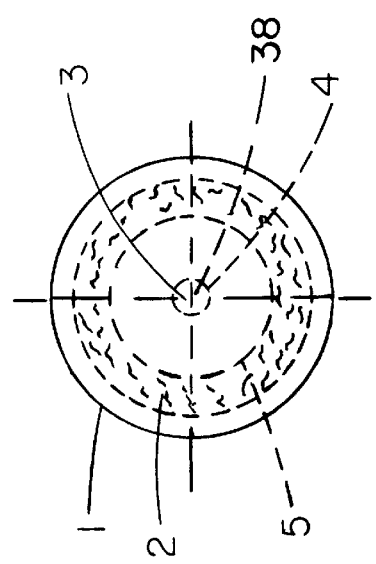
FIG. 3 is a distal end perspective view of the external penile prosthetic device showing the widest extent along plane B.
Figure 4:
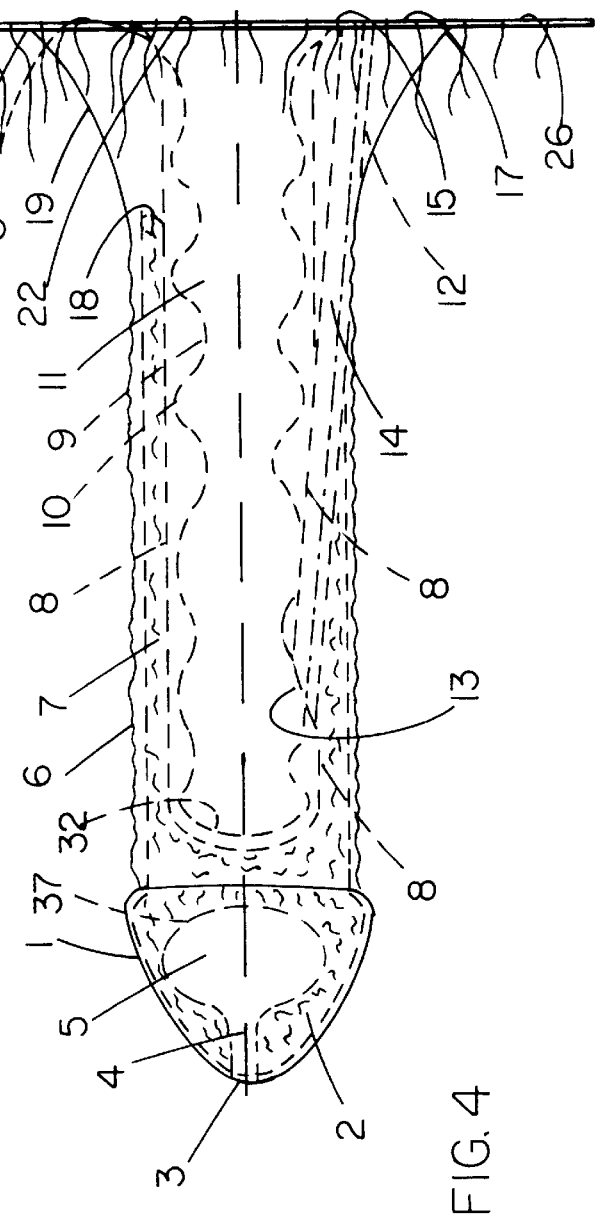
FIG. 4 is a side perspective view of the external penile prosthetic device constructed according to the principles of this invention.
Figure 5:
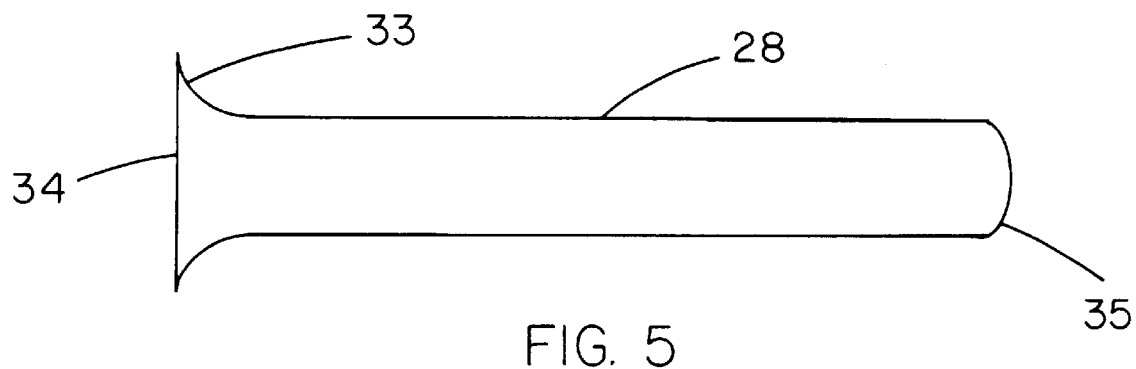
FIG. 5 is a side perspective view of the solid, cylindrical obturator that fits into the internal chamber.
Figure 6:
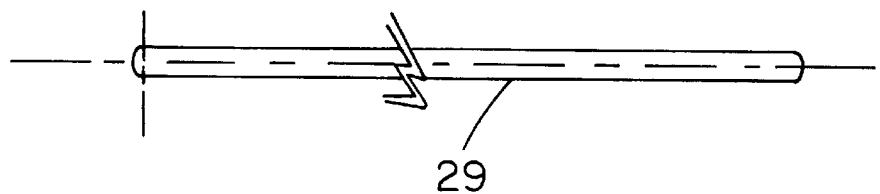
FIG. 6 is a side perspective view of the solid, flexible, cylindrical insertion rod.
Figure 7:
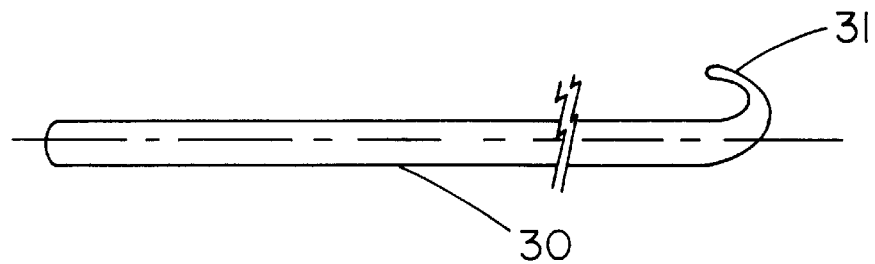
FIG. 7 is a side perspective view of the solid, stiff, cylindrical extraction rod.

An external penile prosthetic device constructed according to the principles of this invention is shown in FIGS. 1, 4, and 8 as it would appear when unattached to the body. The device is one piece as it appears in FIG. 1 that is comprised of multiple walls 8, 6, 1, and 37. Walls 8 and 6 are fused at the top end which flares outward in conical fashion 19 as fusion takes place and ends in a smooth surfaced flange 20, 7½" in its greatest diagonal distance, that has 4 sections; an anterior symphysis pubis portion 25, 6" wide by 2" high from the inner chamber entrance 22; a right adductor groin lobe 27 and a left adductor groin lobe 26, both 6" long by 2½" at their individual greatest width, and a small posterior bridging section 17, ½" wide. As fusion takes place, the conical expansion 19 which is 1¾" high extends 360 degrees around the proximal, top section ending in the flange 20. This conical expansion 19 is thickened, very firm silicone that buttresses the device, so as to function as a compressive force diffuser, and as it extends to the periphery of its base 24, 36, begins to thin down markedly to form an attenuated wafer thin apron 21, ¾" to 1" wide of silicone that extends completely around the total periphery of the flange 20, but not extending from the posterior bridging section 17. The periphery of the thickened flange cone 19 is smoothly curved inward at 24 and 36 to allow contouring around the adductor tendons. The side to side dimension of flange 20 and apron 21 is approximately 6". The front to back dimension of both adductor lobes 26 and 27 is also 6". In the center of the flange 20 is located the entrance 22 of the inner chamber 11. Both the entrance 22 and diameter of the inner chamber 11 measure the same at 1½". Posterior to the center of the entrance 22 of the inner chamber 11 is the entrance 15 measuring 5/16" diameter to the flexible rod insertion tunnel 12, 5/16" diameter which resides in the posterior bridging section 17.

This entrance 15 is covered by 2 end to end coapting flaps 16 that are part of the smooth surface of the flange 20. These flaps 16 have their end to end coaptation 39 oriented in the anterior-posterior direction and permit entrance to the tunnel 12 of the flexible rod 29, 4/16" diameter by 24" long but upon rod 29 removal, close to prevent the medical adhesive from entering the tunnel. Imbricated and woven into the conical expansion 19 and the side of the flange 20 facing away from the body interface is a plurality of filaments 23 which may be real hair or polymer fibers.

The cylindrical total containment wall 6 begins its uniform outer diameter dimension of 2¼" at a point about 1¾" from the smooth flange surface 21 which is equal to the height of the conical expansion 19. The total containment wall 6 then extends distally a length of 8 to 10 inches depending on preference and terminates in a smoothly pointed, mushroom shaped expansion which is the penile prosthetic device head 1 which measures 2 9/16" in its greatest diameter and 1¾" in height. The thickness of the total containment wall 6 and the penile prosthetic device head 1 is ⅛".

Beginning at its entrance opening 22 in the attachment flange 20 the inner chamber 11 extends distally for 7 inches in a centrally located position within the inner wall that is concentric and completely enveloped by the total containment wall 6. The distal extent of the inner wall 8 ends in a totally sealed, blunted, round configuration. The outer surface of the inner wall 8 is smooth with an inner surface comprised of crenulated peaks 9 and valleys 10 rising and falling variable distances of ⅛" for valleys 10 and ¼" to ⅜" for peaks 9. These peaks 9 and valleys 10 are usually but not consistently aligned so that peaks 9 oppose peaks 9 and valleys 10 oppose valleys 10 as this configuration extends 360 degrees around the entire inner wall 8 and represent vaginal rugae.

Extending from its entrance opening 14 on the smooth flange 20 surface of the posterior bridging section 17, the flexible rod tunnel 12 extends in slightly oblique manner through the conical expansion 19, positioning between the outer aspect of the inner wall 8 and the smooth inner aspect of the total containment wall 6; and coursing on the posterior aspect of the inner wall 8, so as to terminate its extent through its exit opening 13 inside the inner chamber 11 about 1½" from the blunt end of the inner wall 8.

Between the cylindrical inner wall 8 and the cylindrical total containment wall 6 is a chamber 7 that is totally sealed at one end 18 by the beginning of the conical fusion 19 of the inner wall 8 and total containment wall 6; and at the other end by the wall of the penile prosthetic device head 1. This chamber 7 extends 360 degrees totally enveloping the inner wall 8 and contains a gel form of silicone similar to that used by the Mentor and McGhan companies and others in their breast implants that is allowed to free flow throughout the entire extent of the chamber 7 from fusion seal 18 to the tip of the penile prosthetic device head 1 where the distal most extent of chamber 7 becomes chamber 2.

Within the head 1 of the penile device centrally located, is a spherical cavity wall 37, about 1½" in diameter and 1/64" thick that is contiguously connected with the wall 1 of the penile prosthetic device head by means of an inward invagination of the wall 1 creating a flap type exit for the spherical cavity chamber 5 called the urethral flap slit 38 which is ¼" diameter with end to end flap coaptation aligned anterior to posterior. External compression of the total containment wall 6 at the upper end or mid portion of its length will create a transmitted positive pressure wave in the silicone gel in chamber 7 that will propagate distally into chamber 2 of the penile prosthetic device head. Since chamber 7 and chamber 2 are continuous and totally contained, the pressure will be transmitted to the area of least resistance which is the spherical cavity wall 37 causing the spherical cavity chamber 5 to collapse and forcing its contents through its narrow exit connection 4, ¼" in diameter through the urethral flap slit 38, to the outside of the device with a small short gush because of Bernoulli's Principle. When no pressure is applied, the urethral flap 3 restrains the contents of the spherical cavity chamber 5 and prevents external release of the contents of the spherical cavity chamber 5 assuming the contents are of a gelatinous or creamy consistency such as sperm or K-Y Jelly, etc. The spherical cavity chamber 5 is loaded by using either a small bulb syringe or an extended nose syringe without needle, both of which are easily obtainable commercially.

To assist wearers with considerable flaccidity to enter the penile device, a flexible silicone rod 29 is introduced through the opening 15 of tunnel 12, passed into the end of the inner chamber 11 and retrieved out of the inner chamber 11 by the stiff silicone extraction rod 30 which is 12" long by ⅜" diameter and cradles the flexible rod 29 with its hook 31. The hook 31 is blunt and smooth tapering to a round terminus ⅛" diameter with inner curve diameter of 5/16" and outer curve diameter of ⅞", Small pieces of commercially available tape secure the end of the penis to the end of the flexible rod 29 which is then withdrawn from the tunnel 12 pulling the penis its full length into the inner chamber 11. For wearers with no penis an obturator 28, 7" long by 1" diameter, which is made of stiff silicone is inserted into the inner chamber 11 until its smooth beveled surfaces 34, 33, 35, are flush with the inner chamber 11 opening 22, and distal end 32.

Except for the plurality of filaments 23 which may be either real pubic hair or polymer fibers commercially available, the entire penile prosthetic device is preferably made of silicone in various stages of curing. Positive and negative molding techniques are used to produce the exact device components from silicone such as but not limited to Silicone (A-595) made by Factor 2 Company in Arizona. The molds are made by creating the penile image as a wax model first, then producing the negative in "dental stone". Curing techniques determine the stiffness or flexibility of the silicone. The gel form for free flow in chambers 2, 7 of the penile prosthetic device is preferably medical grade silicone gel similar to that used in the manufacture of breast implants although in this case, no gel is being implanted in the body. The firmness of the erection is attained by the firmness of the outer total containment wall 6 plus the firmness of the inner wall 8 plus the totally contained silicone gel in chambers 7 and 2 acting in consort to produce a summation effect supporting each other and thus the total construction of the device. Should the improbable event of a silicone gel leak occur using the penile prosthetic device, the gel would simply exit the vagina during and after intercourse making any medical problem caused by a silicone gel leak nonexistent since the medical grade silicone gel itself is essentially inert especially when not contained or trapped in the body.

OPERATION

BEFORE applying the penile prosthetic device, it is imperative that the wearer completely shave the region of the groin, symphysis pubis and inner aspect of both thighs as failure to do so results in a painful application and removal of the device in addition to producing poor adhesion at the device-body interface. The above mentioned body parts must be free of moisture and completely dry before the device is applied.

Application then begins by inserting the flexible silicone insertion rod 29 into the small flapped tunnel entrance 15 that resides behind the entrance to the inner chamber 22. The rod 29 is advanced distally until it almost exits the distal opening 13 of the tunnel 12. The extraction rod 30 is then inserted into the opening 22 of the inner chamber 11 entering the hook portion 31 first and then advancing the extraction rod 30 until the hook 31 gently rests on the most distal end 32, of the inner chamber 11. The flexible rod 29 is further advanced until it completely exits the tunnel exit 13 and begins to meet resistance and coil backwards on itself at the bottom of the inner chamber 11. The extraction rod 30 is then used to cradle the flexible rod 29 as it is coiling and being further advanced. The flexible rod 29 is then guided by the extraction rod 30 as the flexible rod 29 advancement is continued and the extraction rod is gradually removed from the inner chamber 11. This process is continued until about 2 inches of the flexible rod 29 protrudes out of the opening 22 of the inner chamber 11, and the other end of the rod 29 also protrudes out of the opening 15 of the tunnel 12.

Two separate pieces of an adhesive tape are attached in parallel fashion to the end of the flexible rod 29, the adhesive surfaces opposing each other but not touching. The end of the penis is then placed between the 2 tapes and secured by the tapes. (It is important to use this configuration of taping as the tape must release the penis when it reaches its maximum advancement into the inner chamber 11.)

Once the end of the penis is secured to the protruding end of the flexible rod 29 by the tapes, the flexible rod 29 is pulled out of the tunnel 12, thus simultaneously advancing the penis into the depths of the inner chamber 11 to its maximum advancement while the device is held appropriately by its attachment flange 25 in order to help guide the penile advancement. Constant application of an increasingly stronger force to the flexible rod 29 exiting from the tunnel 12 at its opening 15 will release the tapes from the penis allowing the tapes and flexible rod 29 to be completely removed from the penile prosthetic device. A strong medical adhesive such as that made by the Hollister Company, number 7730, is then applied to the entire surface 21 of the attachment flange 25, 26, 27, 17 and the opposing body part of the wearer. When each surface begins to get slightly sticky, the surface 21 of the flange 25, 26, 27, 17 with its adhesive applied is then firmly and constantly pressed against the appropriate body parts of groin, and symphysis pubic region.

In a few minutes, the interface will create a firm bonding which will hold the penile prosthetic device securely in place.

1. If only the erectile properties of the penile device are desired by the wearer, then the device is ready to use at this point.

2. If protection against pregnancy and disease are desired by the wearer, then the device is also ready to use as the inner wall 8 is essentially an elaborate condom.

3. If pregnancy is desired, and insemination of the female in a more natural way is also desired, then prior to all the previously mentioned steps of operation, the sperm of the male is introduced via a small bulb syringe through the urethral flap slit 38 at the distal tip of the penile prosthetic device head 1 directly into the spherical cavity chamber 5. The urethral flap 3 retains the sperm once the sperm has been placed in the spherical cavity chamber 5. Insemination of the female is accomplished during normal intercourse when either the male or female applies firm pressure to the total containment wall 6 of the penile prosthetic device thus creating a positive pressure wave to the silicone gel. This pressure wave is transmitted distally into the head I of the penile prosthetic device which collapses the spherical cavity wall 37 and forces the contents (sperm) residing in the spherical cavity chamber 5 to exit via the urethral slit 38 directly into the female.

4. With advancing age, many females lose the normal lubrication ability of the vaginal vault. The spherical cavity chamber 5 may also be used to contain lubricant and hormonal compounds which can be deposited naturally during intercourse to decrease female pain during intercourse due to a dry vaginal vault.

5. The spherical cavity chamber 5 may also be used to contain medications of various types such as anti-fungal creams, etc, that also may be deposited into the female during the normal sex act while the male is protected by the condom property of the penile prosthetic device.

Removal of the penile prosthetic device is easily accomplished using a medical adhesive remover such as that made by the Hollister Company, number 7731.

Cleaning the penile device is accomplished using an antiseptic soap such as Betadine and water.

What is claimed:

1. An external penile prosthetic device adapted to be worn on the groin and suprapubic areas of the wearer, comprising:
   a generally tubular outer wall made from a flexible material, having an open proximal end and a closed distal end, the exterior of the outer wall configured to resemble an erect human penis;
   a generally tubular inner wall, made from a flexible material, having an open proximal end and a closed distal end, the inner wall being disposed spacedly and coaxially inside the outer wall and sealed thereto at least at their respective proximal ends to define a chamber therebetween;
   a viscous fluid in the chamber between the outer wall and the inner wall; and
   a flange disposed around and connected to the proximal end of the outer wall of the prosthetic device for mounting the device over the groin and suprapubic areas of the wearer.

2. The external penile prosthetic device according to claim 1 wherein the viscous fluid is a silicone gel.

3. The external penile prosthetic device according to claim 1 wherein the outer wall is made from a silicone configured to resemble human skin.

4. The external penile prosthetic device according to claim 1 wherein the interior of the inner wall has a crenulated configuration.

5. The external penile prosthetic device according to claim 1 wherein the interior of the inner wall has irregular surface of raised and recessed areas.

6. The external penile prosthetic device according to claim 1 further comprising a cavity formed in the distal end of the outer wall, the cavity having a relatively large body and a narrow neck communicating with the exterior of the prosthetic device by a slit.

7. The external penile prosthesis according to claim 6 wherein the cavity formed in the distal end of the outer wall projects proximally into the chamber defined between the tubular inner wall and the tubular outer wall.

8. The external penile prosthetic device according to claim 6 wherein the slit is closed with a flap.

9. The external penile prosthetic device according to claim 1 wherein the flange tapers in thickness radially outwardly, away from the outer wall.

10. The external penile prosthetic device according to claim 1 further comprising a plurality of filaments formed on the flange.

11. The external penile prosthetic device according to claim 10 wherein the filaments are hair.

12. The external penile prosthetic device according to claim 10 wherein the filaments are polymer fibers.

13. The external penile prosthetic device according to claim 1 further comprising a passage extending through the chamber, the passage having a proximal end opening in the flange, and a distal end opening in the inner wall inside the prosthetic device.

14. The external penile prosthetic device according to claim 13 wherein the proximal end opening in the flange is closed with a flap.

15. The external penile prosthetic device according to claim 1 further comprising a rigid obturator adapted to be fit inside the prosthesis hollow inner wall to make rigid the prosthetic device.

16. The external penile prosthetic device according to claim 1 wherein the flange is of one piece "U" shaped configuration comprised of two lobes and a connecting segment at one end.

17. The external penile prosthetic device according to claim 1 and further comprising an optional adhesive applied to the proximal side of the flange for attaching the flange to the groin and the suprapubic areas of the wearer of the device, to thereby retain the device in operative position.

18. The external penile prosthetic device according to claim 1 wherein the proximal end of the innerwall is connected to the proximal end of the outer wall in a fluid-tight manner, so that the chamber containing the viscous fluid is completely sealed off at the proximal end by the fusion of the inner wall to the outer wall and at the distal end of the prosthetic device between the closed distal end of the inner wall and the closed distal end of the outer wall.

19. The external penile prosthetic device according to claim 1 wherein the chamber defined between the inner wall and the outer wall is continuous and uninterrupted entirely around the inner wall and extends beyond the closed distal end of the inner wall, so that the viscous fluid in the chamber has free flow capacity 360 degrees around the inner wall the full length of the chamber, and beyond the closed distal end of the inner wall into the closed distal end of the outer wall.

20. A method of inserting a penis into a hollow elongate penile prosthetic device having an inner wall, an outer wall, and a passage extending between the inner wall and outer wall, the passage being open at the proximal end to the exterior of the prosthetic device, and at the distal end to the interior of the device, the method comprising the steps of:
   inserting a tether through the passage from the proximal end to the distal end, through the interior of the prosthetic device to the exterior;
   temporarily attaching the penis to the tether with at least two strips of tape on opposite sides of the penis; and
   pulling the tether to pull the penis into the prosthetic device.

21. A method of expelling contents from the external penile prosthetic device of claim 1, the device having a cavity in the distal end of the outer wall of the device, the cavity having a relatively large body and a narrow neck communicating with the exterior of the prosthetic device by a slit, the method comprising the steps of:

applying a compressive force to the outer wall of the prosthetic device, transmitting the compressive force by the viscous fluid as a positive pressure fluid wave moving distally and coaxially in the chamber between the inner and outer walls of the prosthetic device; and collapsing the body of the cavity by the positive pressure fluid wave pushing cavity contents through the narrow neck and slit to the exterior of the prosthetic device, whereby the cavity can be filled with a preselected fluid and such fluid can be expelled at a preselected time to provide lubrication, medication and insemination, as suits the needs of the wearer of the device.

* * * * *

UNITED STATES PATENT AND TRADEMARK OFFICE
CERTIFICATE OF CORRECTION

PATENT NO. : 5,842,970
DATED : December 1, 1998
INVENTOR(S) : LAKUSIEWICZ, Ronald J.

It is certified that error appears in the above-identified patent and that said Letters Patent is hereby corrected as shown below:

IN THE CLAIMS:

Claim 15, line 3, delete --prosthesis hollow--.

On the title page, item [57]:

IN THE ABSTRACT:

Lines 7 and 8, delete --having a different degree of durameter firmness than that of the outer wall--.

Signed and Sealed this

Sixth Day of July, 1999

*Attest:*

Q. TODD DICKINSON

*Attesting Officer*     *Acting Commissioner of Patents and Trademarks*